United States Patent [19]
Lamphere

[11] 3,964,037
[45] June 15, 1976

[54] FUEL TANK ALARM SYSTEMS

[75] Inventor: David A. Lamphere, Milton, Vt.

[73] Assignee: Simmonds Precision Products, Inc., Tarrytown, N.Y.

[22] Filed: Sept. 5, 1974

[21] Appl. No.: 503,440

[52] U.S. Cl. .............................. 340/244 R; 73/32 R; 73/304 C; 340/236
[51] Int. Cl.² .......................................... G08B 21/00
[58] Field of Search ...................... 340/244 R, 236; 73/304 C, 32 R; 324/61 R

[56] References Cited
UNITED STATES PATENTS
3,801,902  4/1974  Horowitz ........................... 324/61 R

*Primary Examiner*—John W. Caldwell
*Assistant Examiner*—Daniel Myer
*Attorney, Agent, or Firm*—Edwin E. Greigg

[57] ABSTRACT

A fuel tank alarm system comprises three density sensors disposed at different heights within a fuel tank. An electrical density signal produced by the lowest sensor is subtracted from the corresponding signals from the upper two sensors to produce two density-difference signals which are then compared with a reference signal. When an inverse density gradient of dangerous proportion exists in the fuel tank, one or both of the density-difference signals exceeds the reference signal in magnitude and an alarm circuit is actuated. The alarm circuit can automatically start a pump to circulate fuel in the tank and reduce dangerous density inversion of fuel therein.

13 Claims, 2 Drawing Figures

FUEL TANK ALARM SYSTEMS

BACKGROUND OF THE INVENTION

This invention relates to methods and alarm systems for detecting, by density measurement, dangerous stratification of fuel in a fuel tank.

There has been previously proposed a fluid density measuring system for continuously monitoring the density of a fuel in a fuel tank. Such a system comprises a capacitance transducer disposed inside a fuel tank and connected to electronic circuitry which measures the capacitance of the transducer (which is an effective measure of fuel density) and outputs a signal proportional to the fuel density. There is, however, no provision in such a system for comparison of the density of the fuel at several heights within the fuel tank, and dangerous stratification of the fuel can arise without any direct indication being given by the system.

OBJECT OF THE INVENTION

It is thus an object of the invention to provide a density measurement alarm system to warn against dangerous stratification of fuel in a fuel tank, and to provide a method of detecting such stratification.

SUMMARY OF THE INVENTION

According to the invention, there is provided a system for indicating an abnormal density variation in a mass of liquid, comprising at least two density sensors mounted for immersion in the liquid at different respective heights to produce respective output signals each dependent on the density of the liquid at the said respective height, means connected to receive and compare the said output signals whereby to produce an output indicative of the density gradient in the liquid, and alarm means responsive to the density gradient-indicating output to produce an alarm indication when the said output indicates an inverse density gradient in the liquid exceeding a predetermined value.

According to the invention, there is also provided a system for indicating an abnormal density variation in a mass of liquid, comprising first, second and third density sensors mounted in that order for immersion in the liquid at successively higher positions to produce respective output signals each dependent on the density of the liquid at the said respective height, a first difference circuit connected to receive and compare the output signals of the first and third density sensors to produce a first density-difference signal, a second difference circuit connected to receive and compare the output signals of the first and second density sensors whereby to produce a second density-difference signal, and alarm means connected to the first and second difference circuits to receive and monitor the density-difference signals to produce an alarm indication when either one of the said density difference signals exceeds a predetermined value corresponding to dangerous density inversion of the said mass of liquid.

According to the invention, there is further provided a method of detecting dangerous conditions within a fuel tank, comprising the steps of sensing the density of fuel within the tank at at least two different heights and producing respective density signals in correspondence to the fuel density at the respective heights, comparing the said density signals with each other to produce density-difference signals proportional to the density gradient existing in the fuel tank, and monitoring the density-difference signals whereby to activate an alarm when the value of a said density-difference signal corresponds to dangerous density inversion of fuel within the fuel tank.

BRIEF DESCRIPTION OF THE DRAWINGS

An alarm system embodying the invention, and a method according to the invention, both for detecting dangerous fuel stratification in a fuel tank by density measurement, will now be particularly described, by way of example, with reference to the accompanying diagrammatic drawings in which.

DESCRIPTION OF THE PREFERRED EMBODIMENT

Fuel, and particularly liquid natural gas (L.N.G.), left in storage tanks in a static condition for a period of time may develop inverse density stratification which can give rise to a "rollover phenomenon", an extremely dangerous condition causing a large scale boil-off and tank over-pressure.

The method of detecting such dangerous stratification, now to be described, involves measuring the fuel density at three separate tank levels and comparing the density measurements to detect when the inverse density gradient within the tank exceeds a predetermined value. If too large an inverse density gradient is present, impending "rollover" can be manually or automatically prevented by pump circulation.

Figure 1:
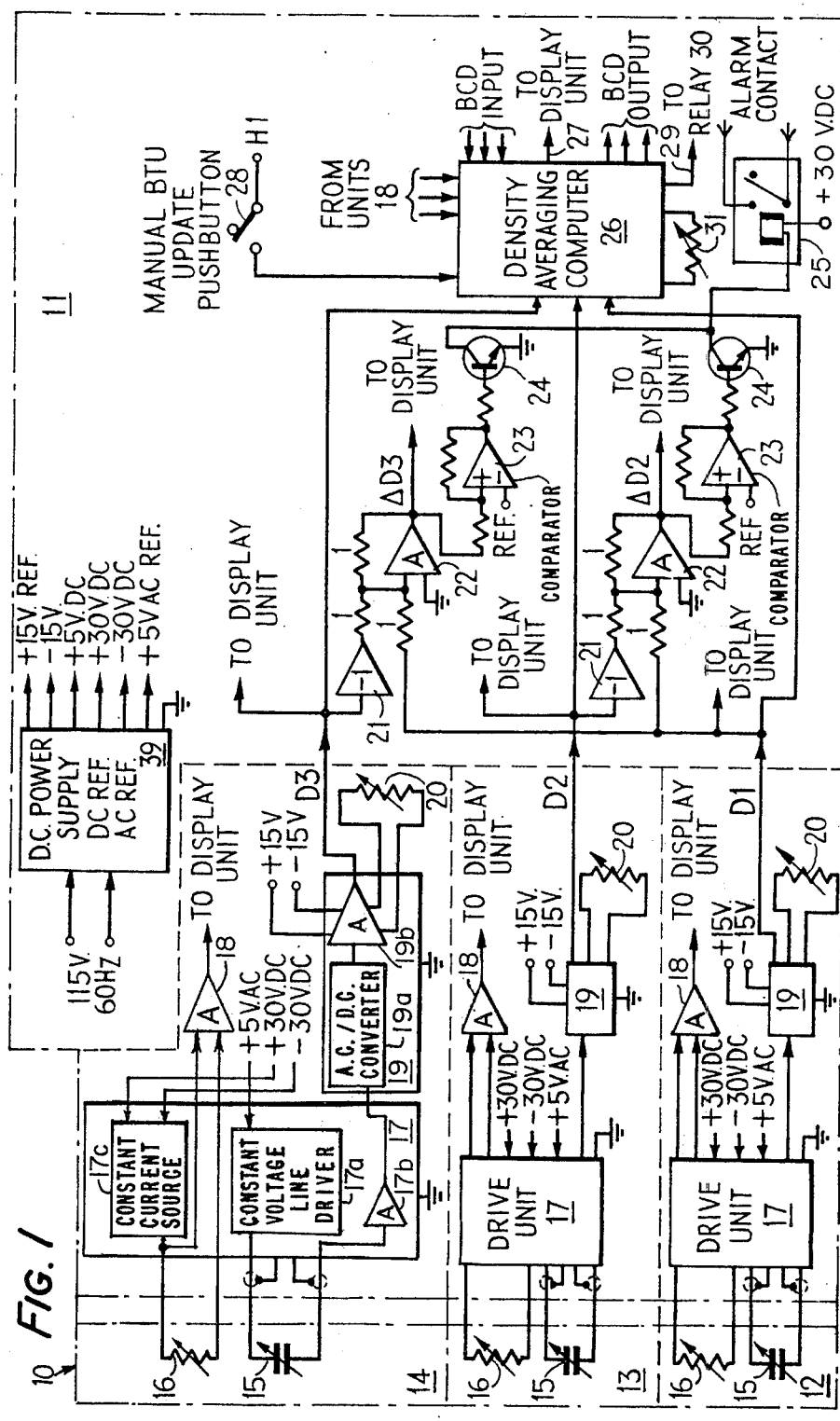
FIG. 1 is a block diagram of a tank unit and a signal conditioner of the alarm system.

As shown in FIG. 1, in the alarm system to be described, a tank unit 10 and a signal conditioner 11 of the alarm system make up three identical density measurement channels 12, 13 and 14, arranged to measure the density of fuel within a tank at different respective heights.

The tank unit 10 comprises for each channel, a density sensor in the form of a capacitive probe 15, whose capacitance varies in correspondence with density variations of the fluid in which it is immersed, and a liquid-level point sensor 16 mounted just above the probe 15. The purpose of the sensors 16 is to indicate whether the corresponding probes are completely immersed in fuel or not; this is necessary to warn against faulty density information from a partially immersed probe. The sensors 16 can be of thermistor type which provide a significant change in voltage drop thereacross between a liquid-immersed and a liquid-free condition.

The signal conditioner 11 comprises, for each channel, a drive unit 17 for driving both the corresponding probe 15 and sensor 16. The unit 17 is intrinsically safe against over-currents, excess voltages and other potentially dangerous electrical faults. An exemplary form of drive unit 17 is shown in FIG. 1 with respect to channel 14, and comprises a line driver 17a arranged to supply a constant A.C. voltage across the corresponding probe 15. The resultant A.C. current through the probe varies as the probe capacitance varies. The probe 15 is connected to an A.C. amplifier 17b of the drive unit 17 which amplifies the probe current. The output of the amplifier 17b is connected to a density output unit 19 which can comprise (as shown with respect to channel 14 in FIG. 1) an A.C./D.C. converter 19a feeding a scaling amplifier 19b. The amplifier 19b is provided with an offset adjust potentiometer 20 to enable accurate setting up of the unit 19.

Figure 2:
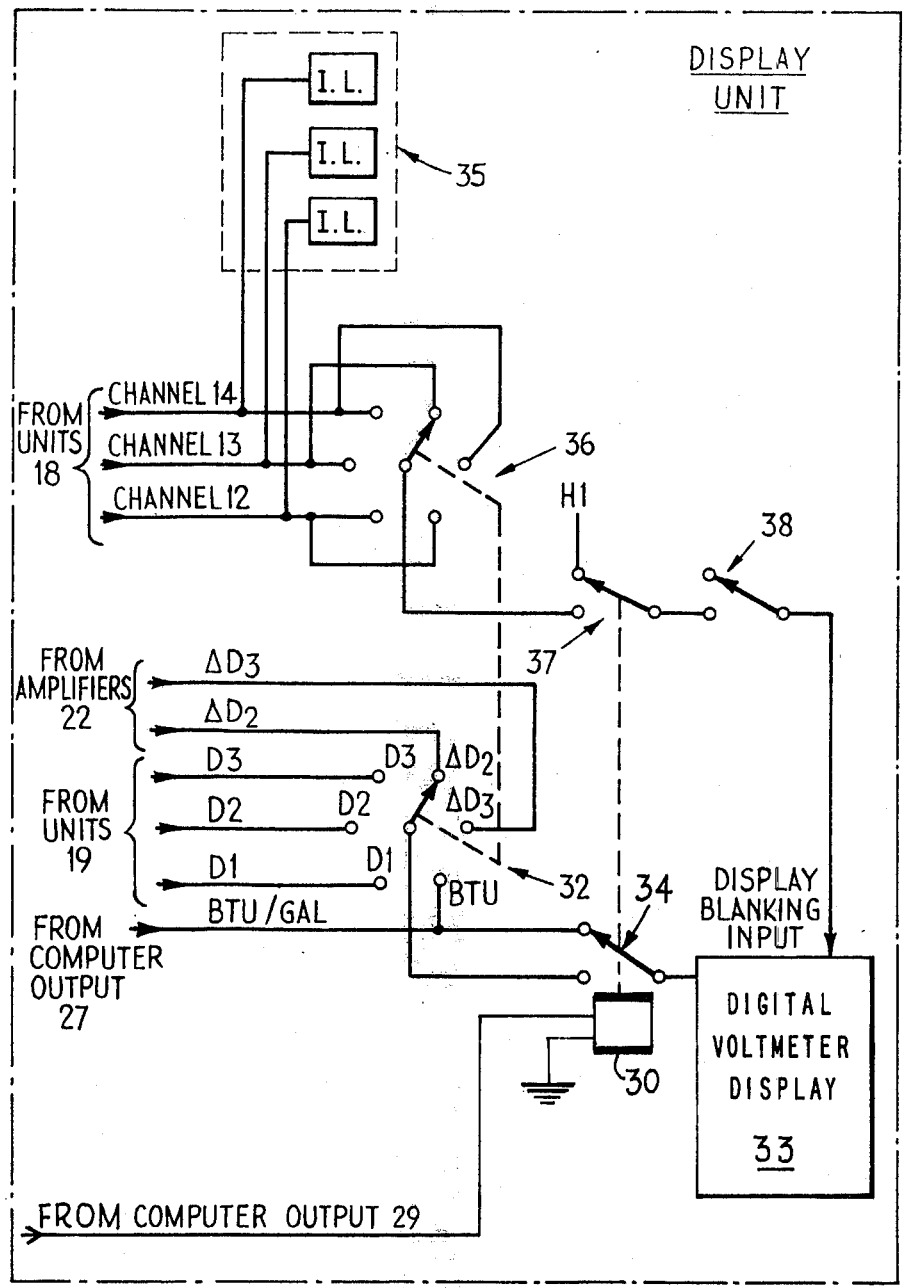
FIG. 2 is a block circuit diagram of a display unit of the alarm system.

The drive unit 17 shown for channel 14 in FIG. 1 further comprises a constant-current source 17c connected to the corresponding sensor 16 for driving a constant current through the sensor. The voltage drop produced across the sensor 16 as a result of current therethough is fed to a level-sensor output unit 18 which can take the form of an amplifier. The outputs of the units 18 are connected to the display unit (FIG. 2) to indicate the state of immersion of their corresponding sensors 16 (and thereby provide an indication of the state of immersion of the probes 15).

The drive units 17 and the output units 18 and 19 of the channels 12 and 13 can be identical to the corresponding units of channel 14 shown in FIG. 1.

The outputs of the three units 19 of the three channels 12, 13 and 14 are connected to the display unit (FIG. 2) and carry D.C. density signals D1, D2 and D3, representing respectively the density of fuel at a lower, center and upper probe level within the fuel tank. The signal conditioner 11 is arranged to compare continuously the density signals to provide two density difference signals $\Delta D2$ and $\Delta D3$ corresponding to (D2-D1) and (D3-D1) respectively. This is carried out in two identical subtract units each of which comprises an inverter 21 to invert one of the D2 or D1 (or, D3 or D1) relative to the other, and a unity-gain, inverting, summing amplifier 22 to sum at its input the inverted one of the two signals and the other signal to give an output signal corresponding to $\Delta D2$ (or $\Delta D3$).

The outputs of the amplifiers 22 are connected to respective comparators 23 to enable the two signals $\Delta D2$ and $\Delta D3$ to be compared with a reference signal. The comparator outputs are connected via associated driver transistors 24 to an alarm relay 25, thereby to energize the relay and close alarm contact to set off an alarm when either of the signals $\Delta D1$ and $\Delta D3$ exceeds its reference signal which condition indicates that a dangerous density gradient is present in the fuel tank.

A small computer 26 is also incorporated in the signal conditioner 11 for calculating the average of the density measurements and presenting it in B.T.U./GAL. The outputs of the units 19 are connected to the computer 26 as are the outputs of the units 18, the latter to prevent erroneous density averages due to a probe 15 not being fuel-immersed. An output 27 from the computer 26 is connected to the display unit and the computer additionally has binary-coded-decimal (BCD) input and output facilities. The BCD average density output can be fed to a further computer for billing purposes and can be updated either automatically at regular intervals by the computer 26 or when manually initiated using a pushbutton 28. An output 29 of the computer 26 is connected to a relay 30 (FIG. 2) whereby when updating occurs, the updated average density reading can be displayed in a manner to be described. A potentiometer 31 permits correct calibration of the average density reading fed to the display unit.

The display unit (FIG. 2) comprises a six-way rotary switch 32, connected to the outputs of the units 18 and 19, and to the output 27, for selectively feeding to a 5-digit, digital voltmeter display 33 one of the readings D1, D2, D3, $\Delta D2$, $\Delta D3$, or B.T.U/GAL. Interposed between the output of switch 32 and the input of display 33, is a two-way single-pole switch 34 controlled by the relay 30 such that when updating of the BCD computer output is occurring, the B.T.U./GAL reading is automatically connected to the display 33 regardless of the switch position of the switch 32.

The outputs of the units 18 are connected to respective display lamps of a liquid-level, point sensor display 35, to indicate the state of immersion of the sensors 16. The outputs of the units 18 are also connected to a second six-way rotary switch 36, ganged to the switch 32, whereby the outputs are selectively fed to a display-blanking input of the display 33 to blank out the reading selected by the switch 32 for display if the state of immersion of the sensors 16 indicate that the reading to be displayed would be erroneous.

Interposed between the output of switch 36 and the display-blanking input of the display 33 is a two-way, single-pole switch 37 and a display-blanking override switch 38. In an open position of switch 38, the display is not blanked. In a closed position of switch 38, blanking of the display 33 is dependent on the signal fed from the output of switch 37, which in a first position is connected to the output of the switch 36 and in a second position to a voltage H1 to effect blanking of the display 33. The switch 37 is ganged with the switch 34 to be in its second position during BCD updating.

A power supply unit 39 is incorporated in the signal conditioner 11 and, in this example, is designed for operation from a mains supply of $11^5 \pm 10v$ A.C. at a nominal 60Hz.

Zener barriers (200 ohms) render the alarm system instantly safe in hazardous areas.

In operation of the described alarm system, A.C. signals from the three probes 15 are fed via their respective units 17 to their respective units 19 which output the corresponding signals D1, D2 and D3. From these signals are derived the density difference signals $\Delta D2$ and $\Delta D3$ which activate the alarm relay 25 on exceeding a predetermined value, i.e., when density inversion in the fuel tank reaches dangerous levels. The relay 25 can be used to start a pump to circulate fuel within the tank, or to set off an audio and/or visual alarm. The signals D1, D2 and D3 are also used to calculate in the computer 26 an average density in B.T.U./GAL.

Use of the switch 32 enables any one of the signals D1, D2, D3, $\Delta D2$, $\Delta D3$ and B.T.U./GAL, to be displayed on the display 33.

The liquid-level point sensors 16 indicate in the display 35 the state of immersion of the probes 15 and prevent presentation on the display 33 of erroneous readings. An uncovered probe 15 will not cause faulty actuation of the alarm relay 25 because the faulty density information is in the "safe" direction from a roll-over standpoint. The blanking override switch 38 enables information from a partially covered probe 15 to be displayed for test purposes.

The system typically measures density to a five digit accuracy in pounds per cubic foot over the full industrial temperature range.

What is claimed is:

1. A system for indicating an abnormal density variation in a mass of liquid contained within a storage tank, comprising:
    at least two density sensing means mounted in said tank at different respective heights for producing respective density output signals proportional to the density of the liquid at each respective height when said density sensing means are immersed in said liquid, at least one density gradient sensing means connected to two of said density sensing means, for comparing the density output signals of the two density sensing means and for producing a density gradient output signal proportional to the density gradient in the liquid between the two density sensing means, and alarm means connected to said density gradient sensing means, for producing an alarm indication when said density gradient output signal indicates an inverse density gradient in the liquid exceeding a predetermined value.

2. A system according to claim 1, wherein said density sensing means comprises a variable-capacitance sensor.

3. A system according to claim 1, which further comprises liquid level sensing means mounted in said tank adjacent and just above respective said density sensing means, for producing respective level signals indicative of the state of liquid immersion of said adjacent density sensing means.

4. A system according to claim 1, in which the alarm means includes
a reference source for producing a reference signal, and
means for comparing said density gradient output signal with said reference signal and for producing said alarm indication when said density gradient output signal exceeds said reference signal.

5. A system according to claim 1, in which said density gradient sensing means comprises:
two scaling amplifier means, each connected to one of the two density sensing means, for producing a corresponding scaled density signal, and
subtracting means, connected to said two scaling amplifier means, for subtracting said scaled density signals one from another thereby producing said density gradient output signal.

6. A system according to claim 5, which further comprises
computing means, connected to receive said scaled density signals, for producing an average scaled density signal for the liquid in the tank.

7. A system according to claim 5, which further comprises
digital display means, and
selecting means, connected between said scaling amplifier means and said display means, for feeding a selected one of said scaled density signals to the display means.

8. A system according to claim 7, wherein said selecting means is also connected to receive said density gradient output signal whereby the density gradient output signal can be selectively fed to the display means for display.

9. A system according to claim 7, which further comprises
liquid-level sensing means, mounted in said storage tank adjacent and just above respective said density sensing means, for producing respective level signals indicative of the state of liquid immersion of said adjacent density sensing means,
display blanking means associated with the said display means, and
control means for said display blanking means, connected to receive said level signals, for blanking the display of any selected scaled density or density gradient signal derived from a density sensing means which is not immersed in the liquid.

10. A system according to claim 9, wherein each said liquid sensing means includes a thermistor.

11. A system for indicating an abnormal density variation in a mass of liquid contained within a storage tank, comprising:
first, second and third density sensors, mounted in that order within said tank for immersion in the liquid at successively higher positions, for producing respective output signals each proportional to the density of the liquid at each respective height,
a first difference circuit connected to said first and third density sensors, for comparing the density output signals of the first and third density sensors and for producing a first density-difference signal,
a second difference circuit connected to said second and first density sensors, for comparing the density output signals of the second and first density sensors and for producing a second density-difference signal, and
alarm means, connected to the first and second difference circuits to receive and monitor the density-difference signals, for producing an alarm indication when either one of the said density-difference signals exceeds a predetermined value corresponding to dangerous density inversion of said mass of liquid.

12. A system according to claim 11, comprising:
three liquid-level, point sensors, each disposed within said tank adjacent and just above a respective one of the said density sensors, for producing a liquid-level signal indicative of the state of immersion of the associated density sensor in the said mass of liquid.

13. A method of detecting a dangerous density inversion of fuel within a fuel tank, comprising the steps of:
sensing the density of fuel within the tank at least two points of different heights and producing respective density signals proportional to the fuel density at the respective heights,
comparing at least one of said density signals with other of said density signals, producing at least one density-difference signal proportional to the density gradient existing in the fuel tank between the two heights corresponding to the two density signals compared, and
monitoring said at least one density-difference signal and activating an alarm when the value of said density-difference signal corresponds to dangerous density inversion of fuel within the fuel tank.

* * * * *